(12) United States Patent
Jiang et al.

(10) Patent No.: US 9,157,894 B2
(45) Date of Patent: Oct. 13, 2015

(54) AUTOMATED ULTRASONIC ELASTICITY IMAGE FORMATION WITH QUALITY MEASURE

(75) Inventors: Jingfeng Jiang, Madison, WI (US); Timothy Jon Hall, Madison, WI (US); Amy Marie Sommer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 371 days.

(21) Appl. No.: 13/607,213

(22) Filed: Sep. 7, 2012

(65) Prior Publication Data

US 2012/0330155 A1 Dec. 27, 2012

Related U.S. Application Data

(63) Continuation of application No. 11/155,950, filed on Jun. 17, 2005.

(51) Int. Cl.
*A61B 5/05* (2006.01)
*G01N 29/06* (2006.01)
*A61B 8/08* (2006.01)
*G01N 29/265* (2006.01)
*G01N 29/50* (2006.01)
*G01S 7/52* (2006.01)

(52) U.S. Cl.
CPC *G01N 29/06* (2013.01); *A61B 8/08* (2013.01); *A61B 8/485* (2013.01); *G01N 29/0609* (2013.01); *G01N 29/265* (2013.01); *G01N 29/50* (2013.01); *G01S 7/52042* (2013.01); *G01N 2291/02475* (2013.01); *G01N 2291/02827* (2013.01); *G01S 7/5205* (2013.01)

(58) Field of Classification Search
USPC .......................................... 600/407, 410, 437
See application file for complete search history.

(56) References Cited

U.S. PATENT DOCUMENTS

| | | |
|---|---|---|
| 6,508,768 B1 | 1/2003 | Hall et al. |
| 6,558,324 B1 | 5/2003 | Von Behren et al. |
| 6,659,953 B1 | 12/2003 | Sumanaweera et al. |
| 2002/0062086 A1 | 5/2002 | Miele et al. |

*Primary Examiner* — Joel F Brutus
(74) *Attorney, Agent, or Firm* — Boyle Fredrickson, S.C.

(57) ABSTRACT

Image data and E-mode images used in ultrasonic elasticity imaging may be automatically evaluated for quality to provide a single value used as operator feedback or for automatic selection of images for averaging or animation.

8 Claims, 3 Drawing Sheets

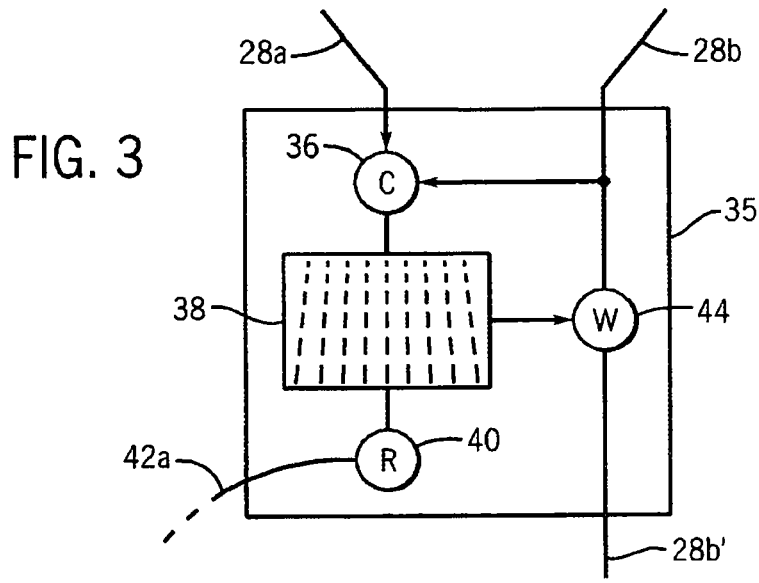
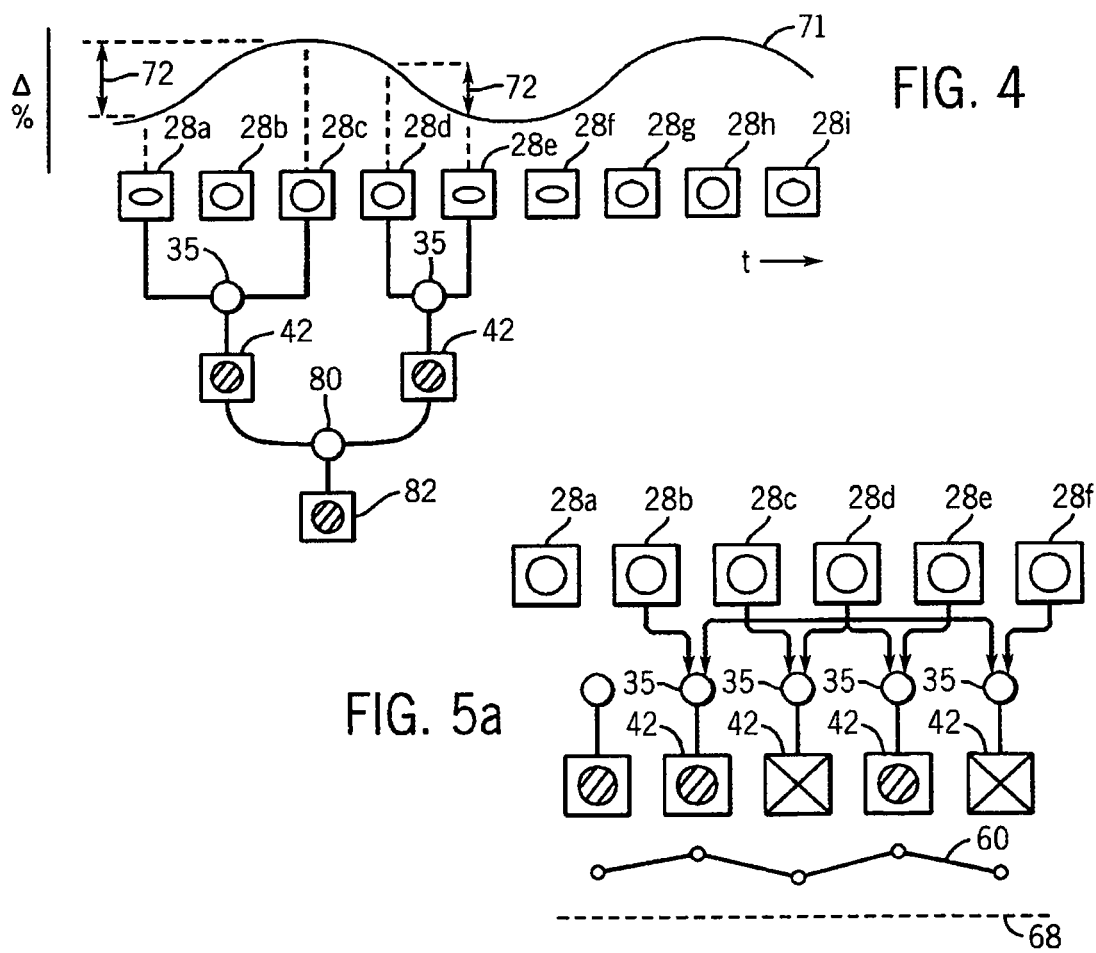

AUTOMATED ULTRASONIC ELASTICITY IMAGE FORMATION WITH QUALITY MEASURE

CROSS REFERENCE TO RELATED APPLICATION

This application is a continuation of U.S. patent application Ser. No. 11/155,950 filed Jun. 17, 2005 and hereby incorporated by reference.

STATEMENT REGARDING FEDERALLY SPONSORED RESEARCH OR DEVELOPMENT

This invention was made with government support under EB002722 awarded by the National Institutes of Health. The government has certain rights in the invention.

BACKGROUND OF THE INVENTION

The present invention relates to ultrasonic medical imaging devices and, in particular, to a method of automatic elasticity image formation in which each elasticity image is accompanied by a quality measure that can be used for the purpose of operator feedback or automatic image selection.

Elasticity (E-mode) imaging reveals the stiffness properties of tissue, for example, strain, Poisson's ratio, and Young's modulus. The stiffness measurements may be collected over an area or volume and then mapped to a gray or color scale to form a two- or three-dimensional E-mode image.

In quasi-static elasticity imaging, images of the tissue in different states of deformation are obtained by ultrasonic or other imaging devices. Strain is deduced from two images by computing a gradient in displacement between the images along any desired direction. Quasi-static elasticity imaging is analogous to a physician's palpation of the tissue during which the physician determines stiffness by pressing the tissue and detecting the amount of tissue yield under this pressure.

The tissue deformation may be obtained manually, for example, by moving the ultrasonic transducer toward and away from the tissue or through a separate compressor mechanism or by physiological movement. Manual deformation of the tissue provides an extremely versatile technique that can be used with standard ultrasonic imaging equipment; however, manual deformation requires considerable operator skill. Ideally, for example, the deformation is at an angle and in an amount to reduce lateral tissue slippage while obtaining appropriate tissue displacement. Too much or too little deformation will not yield consistent E-mode image data.

Often E-mode image data is presented as a time series animation so as to provide an additional dimension of information to the physician. Low quality images incorporated into this animation can create disruptive breaks in the animation obscuring the extra dimension of information hoped to be obtained. Multiple E-mode images may be combined to reduce image noise or provide E-mode measurements along different axes. Again, low quality images incorporated into this combination decrease the quality of the measurement.

SUMMARY OF THE INVENTION

The present invention provides an automatic method of forming E-mode images using quality values that can be employed to provide near real-time operator feedback or an automatic culling of poor images. Importantly, the method operates quickly and may provide a single "quality value" that can be evaluated automatically against a threshold and/or unambiguously displayed to an operator to guide the operator's deformation technique and/or to train operators. In the preferred embodiment, the single quality value is derived from different metrics, each having different strengths.

Specifically, the present invention may provide an E-mode imaging apparatus having a tissue compressor adapted to apply a varying deformation to tissue and an image acquisition system collecting a series of images of the tissue during different stages of deformation by the tissue compressor. An electronic computer receives the series of images to generate a quality value singly indicating a quality of E-mode data obtainable from a currently acquired subset of the series of images. An output of the quality value is provided for use in adjusting or varying deformation to improve the quality of E-mode data.

Thus it is one object of at least one embodiment of the invention to develop a near real-time E-mode formation method where each E-mode image associates with a single scalar measurement that may be used to assess its quality.

It is another object of at least one embodiment of the invention to provide a real-time single quality measurement that may be used to improve the acquisition of E-mode image data.

The present invention may form E-mode images using multiple image signals (as opposed to derived E-mode images) in such a way that guarantees all E-mode images reside in the same physical grid. Composite E-mode images that may have higher signal-to-noise-ratios (SNRs) can be obtained by averaging these E-mode images located in the same physical grid without losing spatial resolution. These composite E-mode images can be displayed for diagnosis or training.

Thus it is another object of at least one embodiment of the invention to provide a method of E-mode image formation by which averaging E-mode images may provide E-mode images with higher signal to noise ratios for diagnosis or training but are not penalized by the reduction in spatial resolution.

The selection of multiple image signals separated by time (as opposed to the derived E-mode images) in the present invention may be rapidly determined to achieve the highest possible quality in the composite E-mode image.

Thus it is another object of at least one embodiment of the invention to provide a method of selecting image signals (as opposed to the derived E-mode images) under which high quality composite E-mode images can be obtained.

The compressor may be manipulable by an operator and the output may be an operator interface providing a representation of the quality value selected from the group consisting of: a displayed number, a displayed visual gauge, a displayed indicator light, and an audio signal.

Thus it is another object of at least one embodiment of the invention to provide a real-time corrective signal to an operator manually deforming tissue to improve the quality of the data acquired.

The compressor may be an ultrasonic transducer and may also provide echo signals for the image acquisition system.

It is thus another object of at least one embodiment of the invention to provide a system that may be used with standard ultrasonic acquisition systems for elasticity measurements.

The quality value may be derived from a comparison of at least one pair of motion corrected images.

Thus it is another object of at least one embodiment of the invention to provide a measurement that may be made directly on the image signals (as opposed to the derived E-mode images) to predict the quality of elasticity information to be obtained therefrom.

The comparison may be a correlation of the motion corrected images.

It is another object of at least one embodiment of the invention therefore to provide a simple mathematical technique for evaluating images that can be sensitive to the entire image area.

The electronic computer may further process the images to create E-mode images located in the same physical grid and the quality value may be derived from a comparison of the E-mode images.

Thus it is another object of at least one embodiment of the invention to provide a measurement that looks directly at the E-mode images to deduce their quality.

The comparison of the E-mode images may be an evaluation of cross correlation or mutual information or other correlation providing a mathematical equivalent of these evaluations of the E-mode images.

It is thus another object of at least one embodiment of the invention to provide a measurement of E-mode images analogous to the measurement of the images used to deduce elasticity information.

The comparison of the E-mode images located at the same physical grid using correlation, mutual information or its mathematical equivalence can reveal the signal-to-noise-ratio (SNR) in their corresponding composite E-mode images.

Thus it is another object of at least one embodiment of the invention to measure the signal-to-noise-ratio of the composite E-mode images formed by the current invention.

The quality value, alternatively or in addition, may be derived from an evaluation of information content of at least one E-mode image, for example, by determining entropy.

It is thus another object of at least one embodiment of the invention to provide a measurement of E-mode image quality that may be obtained from a single image for rapid determination.

The quality value may be based on a single quality metric or may be a combination of two or more different types of measurements of the quality of the E-mode image information.

Thus it is another object of at least one embodiment of the invention to provide a single, quality value deriving from the strengths and benefits of different quality measurement techniques.

The present invention also provides a method of processing a stream of image data to produce E-mode measurements including the steps of: evaluating the stream of images to create a set of corresponding quality values indicating a quality of composite E-mode image data obtainable from the stream of images, and generating output E-mode images using only images associated with quality values over a predetermined threshold.

Thus it is another object of at least one embodiment of the invention to provide for the possibility of automatic selection of images for use in generating elasticity data.

The composite E-mode images may generally be used to form an animation or may be further mathematically combined.

Thus it is another object of at least one embodiment of the invention to provide a method suitable for a variety of different E-mode image output techniques.

The evaluation of the stream of images may include evaluation of pairs of images having different time separations and generating for each pair, and for each time separation, a quality value. The generation of the output E-mode images may then select among the time separations to generate output E-mode images using pairs of images with time separation associated with quality values over a determined threshold.

It is thus another object of at least one embodiment of the invention to provide a method of automatically selecting appropriate time separations to provide improved elasticity data.

The overall evaluation of a stream of E-mode images using quality values may be derived from the quality evaluation for each individual E-mode image to provide additional feedback to operators.

It is thus another object of at least one embodiment of the invention to provide an overall measurement for a sequence of E-mode images obtained from image signals (as opposed to the derived E-mode images) acquired continuously.

These particular objects and advantages may apply to only some embodiments falling within the claims, and thus do not define the scope of the invention.

BRIEF DESCRIPTION OF THE DRAWINGS

FIG. 3 is a detailed block diagram of a motion correction block of FIG. 2 for making motion correction comparison of the image data;

FIG. 4 is a diagrammatic representation of an application of the present invention to automatically select pairs of images using deformation values to obtain high quality E-mode images;

FIG. 5a is a diagrammatic representation of the selection of particular pairs of images based on quality values to obtain high quality E-mode images;

DETAILED DESCRIPTION OF THE PREFERRED EMBODIMENT

Figure 1:
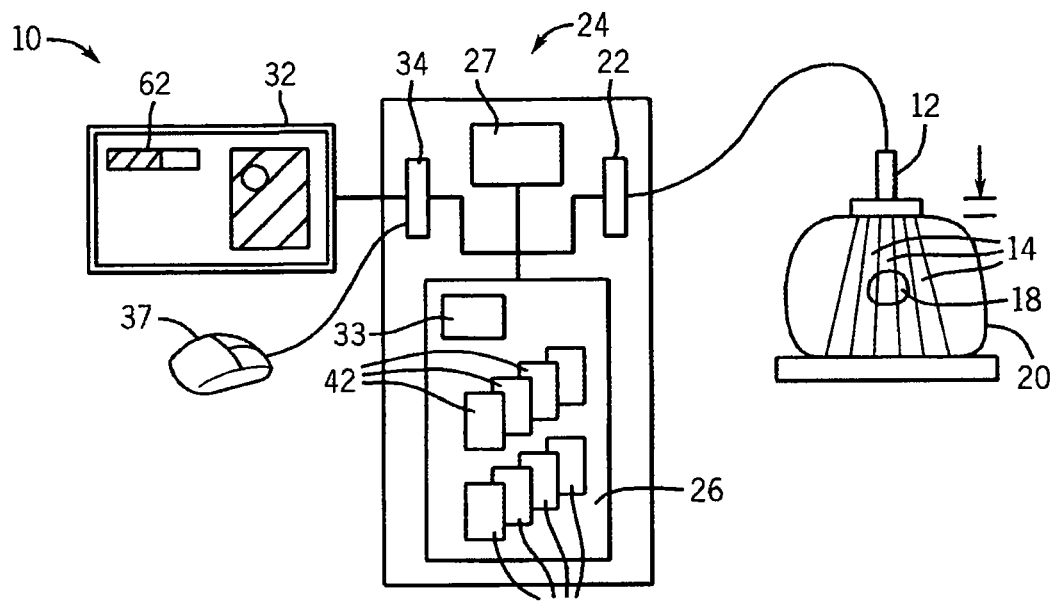
FIG. 1 is a simplified block diagram of an ultrasonic scanner suitable for use with the present invention.

Referring now to FIG. 1 in a preferred embodiment, an E-mode imaging system 10 suitable for use with the present invention provides an ultrasonic transducer 12 which may transmit multiple ultrasonic beams 14 toward a region of interest 18 within a patient 20. The ultrasonic beams 14 produce echoes along different measurement rays passing through volume elements within the region of interest 18.

The echoes are received by the transducer 12 and converted to electrical signals acquired by interface circuitry 22 of a main processor unit 24. The interface circuitry 22 may perform amplification, digitization, and other signal processing on the echo signals as is understood in the art. These digitized echo signals may then be transmitted to a memory 26 for storage and subsequent processing by a processor 27 as will be described. The processor 27 is preferably an electronic computer, a term which, as used herein, encompasses all numeric processing machines providing equivalent function including analog and digital computers as well as specially designed signal processing circuitry.

According to the techniques well known in the art, the stored echo fields 28 may each provide a B-mode image and thus will be referred to generally as image data. Two or more of the echo fields 28 used to form B-mode images are processed to produce an E-mode image 42 according to a stored program 33 held in memory. The B-mode images and the E-mode images 42, both derived from the echo fields 28, may be displayed on an operator display 32 connected with the processor unit 24 by graphic interface 34. The operator display 32 may provide a color monitor and/or a sound output according to techniques well known in the art. The graphic interface 34 may also accept inputs from the keyboard and/or cursor control device 37.

These features are generally available in commercial ultrasound machines such as the Elegra scanner available from the Siemens Medical Solutions, Inc., having a 7.2 MHz linear array transducer operating at 36 MHz in sampling frequency.

Figure 2:
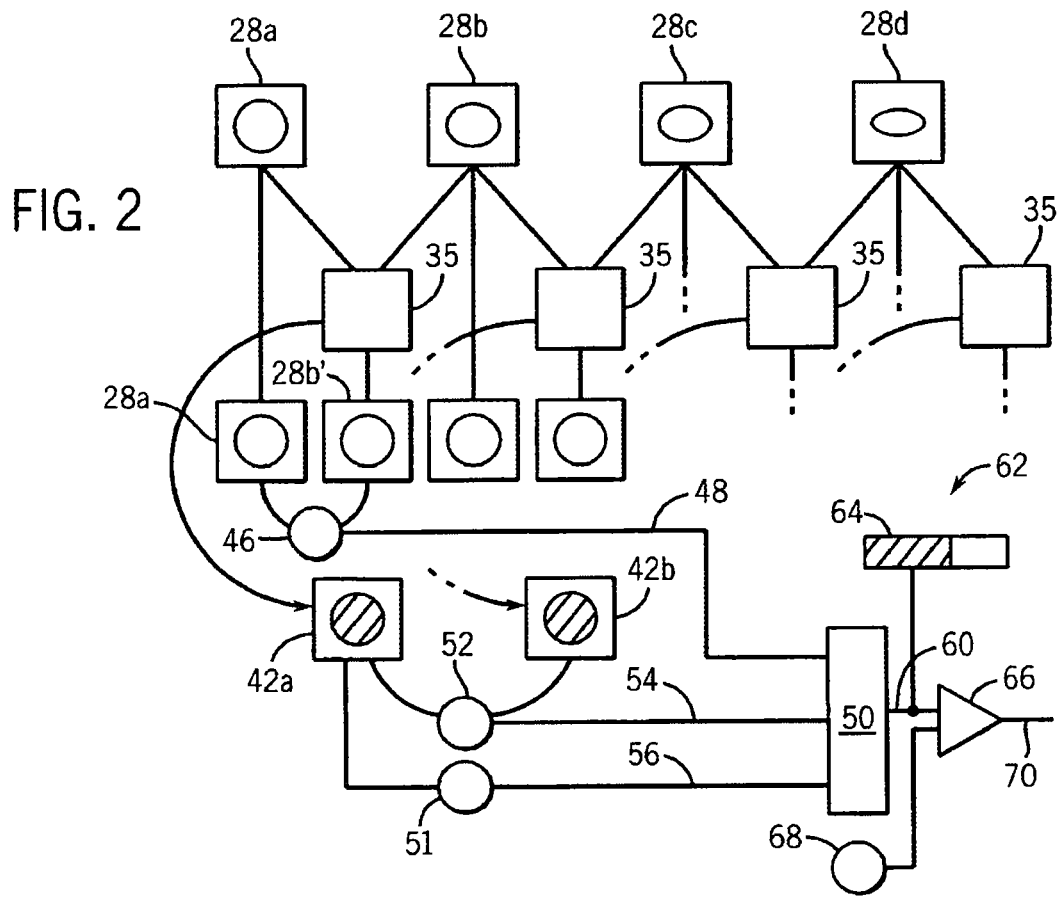
FIG. 2 is a flow diagram showing processing of a series of ultrasonic images obtained from the scanner of FIG. 1 to produce a quality value.

Referring now to FIGS. 1 and 2, the present invention may be implemented in software of the stored program 33 as a series of functional blocks to now be described.

Initially, sequential echo fields 28a through 28d are analyzed in a pairwise fashion (e.g. echo fields 28a and 28b, 28b and 28c, etc.) to estimate displacements, derive E-mode images and to perform an initial E-mode image quality assessment. At a first step in the E-mode image quality assessment, each echo field of the pair, for example, echo fields 28a and 28b are first received by a data warping block 35 which warps the later echo field, in this case, echo field 28b to produce a warped echo field 28b' matching as closely as possible the earlier echo field 28a. Generally each of the echo fields will have been acquired with a different tissue deformation.

Referring also to FIG. 3, the warping block 35 first compares the two echo fields 28a and 28b, as indicated by comparison block 36, to determine a displacement map 38 indicating relative motion between the tissue of the two echo fields 28a and 28b. Calculating such a displacement map 38 is well understood in the art of E-mode imaging and may, for example, be done by making local correlations of the echo fields 28a and 28b within a series of predefined windows over the surface, or volume, of the data to determine local displacement. As will be understood to those of skill in the art, the invention may operate on two or three dimensional echo field acquisitions.

The displacement map 38 is then further processed by the E-mode estimation block 40 to produce an E-mode image 42a. E-mode image formation is well understood in the art of elasticity imaging and may, for example, form strain images by computing the spatial gradient of the displacement field or compute Poisson's ratio or elastic moduli with additional processing, as will be discussed further below.

The displacement map 38 is also received by warped 44 which uses the displacements indicated in the displacement map 38 to warp echo field 28b to approximate the echo field 28a thereby producing motion corrected or warped echo field 28b'.

Referring again to FIG. 2, the unwarped echo field 28a and warped echo field 28b' may then be compared by correlator 46 and the correlation value provides a first quality parameter 48 to be received by combiner 50 to be discussed below. Correlation, as is well understood in the art may measure the sum of the magnitude of the differences between the images on a point-by-point basis over the entire images. Generally this first quality parameter 48 will be sensitive to errors in the displacement map caused by a variety of problems including excessive deformation that moves corresponding tissue outside the analyses window, or by poorly resolved correlation maxima caused by noise or lack of strong echo features in the echo field 28.

This process of determining the first quality parameter 48 is repeated for each sequential pair of echo fields 28 to provide a series of first quality parameters 48 associated with each pair of echo fields 28.

As mentioned above, the E-mode estimation block 40 of the warping block 35 also provides the E-mode image 42a according to techniques well known in the art. Each pair of echo fields 28 processed in this manner will produce one of a series of E-mode images 42a, 42b, etc.

Figure 6:
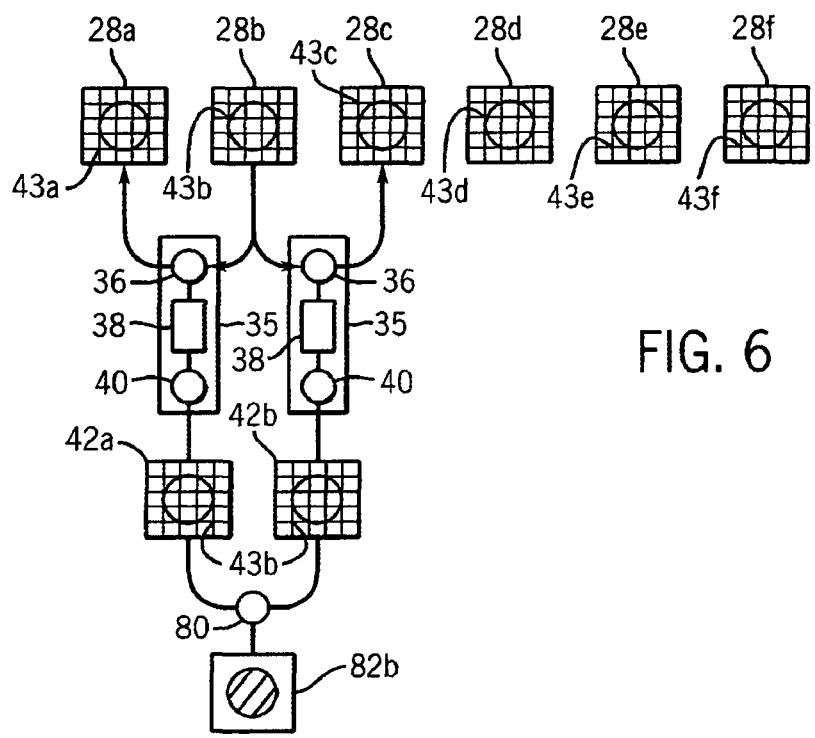
FIG. 6 is a figure similar to that of FIG. 2 showing the preservation of a single physical grid in the combination of image data.

Referring now to FIG. 6, each pair of E-mode images 42, for example, E-mode images 42a and 42b are estimated at the same physical grid 43b. One way to accomplish this goal is to use three echo fields, for instance, echo fields 28a, 28b and 28c. The warping block 35 first compares two echo fields 28a and 28b at comparison block 36 to determine a displacement map 38. The echo fields 28a and 28b are used as target and reference echo fields, respectively. That is, the displacement map 38 indicates a relative motion from the echo fields 28b and its physical grid 43b to the echo fields 28a. Then the E-mode estimation block 40 is used to extract the E-mode image 42a that is mapped into the physical grid 43b of the echo field 28b. As will be understood to those of ordinary skill in the art, this use of the same physical grid is not essential for all embodiments of the invention.

The E-mode image 42b is obtained from the echo fields 28b and 28c following a similar procedure where the echo fields 28b and 28c are the reference and target echo fields respectively to assure that the E-mode image 42b also located at the physical grid 43b of the echo field 28b. The E-mode images 42a and 42b can be combined using the combiner 80 to produce a composite E-mode image 82b by weighted averaging. The composite E-mode image 82b is then on the same physical grid 43b as the reference echo field 28b. The combination procedure is intended to reduce noise and will not degrade spatial resolution in E-mode images (as opposed to temporal smoothing where E-mode images separated by time and referenced to different physical grids are averaged directly).

Referring again to FIG. 2, each pair of these E-mode images 42, for example, E-mode images 42a and 42b, are next compared to determine their similarity by cross correlation (or mutual information or other functionally equivalent comparison) comparison block 52. Mutual information is a well known mathematical technique described, for example, in Introduction to Statistical Communication Theory, by D. Middleton, New York, John Wiley & Sons, 1991, hereby incorporated by reference. The similarity of the two E-mode images 42a and 42b is provided as second quality parameter 54 for each pair of echo fields 28 to be received by combiner 50. The similarity between the two E-mode images 42a and 42b strongly correlates to the E-mode image signal-to-noise-ratio (SNR) of the composite E-mode image 82b (FIG. 6) and the E-mode image SNR can also be used as a second quality parameter 54.

Each E-mode image 42 is also evaluated individually for its information content by means of an entropy measurement, for example, Shannon's entropy also defined in the above-referenced book to provide a third quality parameter 56. Generally, maximum entropy is obtained when all gray (or color) values of the image are equally represented while minimum entropy occurs when the image is of a single brightness. The entropy of the first E-mode image 42a of each image pair is determined by entropy block 51 as third quality parameter 56 received by combiner 50. The third quality parameter 56 may be normalized to a quantity between zero and one.

Each of these quantitative quality parameters 48, 54 and 56 may be combined by combiner 50 which combines the quality parameters 48, 54 and 56 together by an empirically determined equation to produce a single quality value 60.

One realization may be the products of quality parameters 48, 54 and 56.

This single quality value 60 may be displayed by the processor 27 on the operator display 32, for example, in the form of a bar display 62 having a shaded portion 64 that increases to fill the bar of the bar display 62 as the quality value 60 increases. In this way, the operator may be presented with a real-time display of quality value 60 to adjust his or her technique in compressing the tissue using the ultrasonic transducer 12.

Alternative forms of representation including numeric displays, for example, from zero to 100, color displays, tones, or the like may also be used.

Referring now to FIG. 5a, one way of selecting three echo fields, for example, echo fields 28a, 28d and 28f, may be done by using measurements of quality value 60 obtained as described above. For example, a reference echo field 28d may first be selected. Two series of E-mode images can be generated by going backward (for instance, echo fields 28d to 28c, and echo fields 28d to 28b) and forward (for instance, echo fields 28d to 28e, and echo fields 28d to 28f) in time. Then the composite E-mode images 82 can be accepted or rejected depending on the quality value 60 of that triplet of echo fields 28 and their consequent E-mode images 42. Among these echo fields 28 having a quality value 60 greater than the pre-determined threshold 68 for its corresponding composite E-mode image 82, the triplet that has the highest quality value 60 will be eventually selected.

Referring now to FIG. 4, in another application of the present invention, a series of echo fields 28a through 28i may be obtained at different degrees of tissue deformation as indicated by deformation curve 71 providing field averaged strain of the echo fields 28. The processor 27 executing the stored program 33 receiving echo fields 28 may evaluate pairs of echo fields 28 having different time separations. Thus, for example, echo fields 28a and 28c may be compared as well as echo fields 28d and 28e. Generally, each pair of echo fields will provide between them a tissue strain value 72 representing the difference between the values of the deformation curve 71 at the time of the acquisition of the particular echo field 28.

The selection of the particular pairs of echo fields 28a and 28c, for example, may be done by finding comparable tissue strain values 72 or may be done by using a combination of tissue strain and measurements of quality value 60 obtained as described above. For example, pairs of echo fields 28 may first be selected by tissue strain values 72 and then accepted or rejected depending on the quality value 60 of that pair of echo fields 28.

Figure 5B:
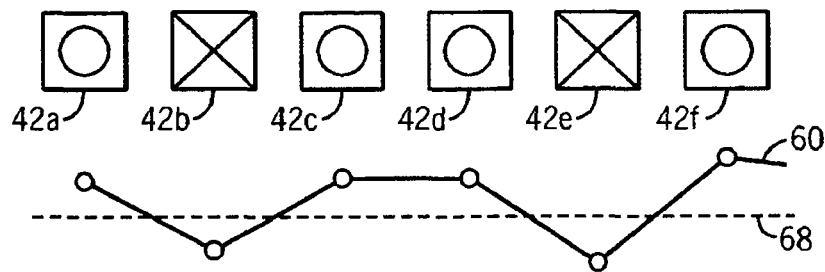
FIG. 5b is a pictorial representation of the selection of particular E-mode images in a time series by use of a quality value obtained by the present invention.

Referring now to FIG. 5b, the quality value 60 may further be used to select only those E-mode images 42 having greater than a pre-determined quality value 60 to be combined by combiner 80 to produce a composite E-mode image 82. The composite E-mode image may produce a superior signal-to-noise ratio when constructed of similar E-mode images 42 or may provide additional dimensions of E-mode measurement, for example, for deformations along different angles or of different amounts.

In this latter regard, referring to FIG. 2, the quality value 60 may be provided to a comparator 66 which may compare the quality value 60 against a threshold 68 to produce a binary acceptance value 70 that may be used for eliminating low quality images on an automatic basis.

Referring now to FIG. 5, this same technique may be applied to a series of E-mode images 42a through 42f as shown in FIG. 5 such as may be output as composite E-mode images in the form of an animation. In this case, the quality value 60 is compared against the threshold 68 and where the quality value 60 drops below the threshold 68 for a particular E-mode image 42b and 42e in this example, those E-mode images are eliminated from the animation.

Figure 7:
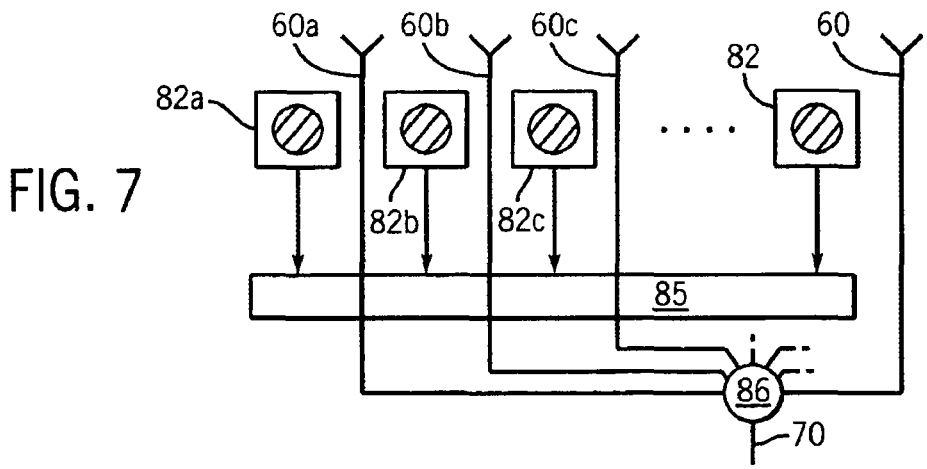
FIG. 7 is a diagrammatic representation of the collection of quality data for a measure of a combined sequence of E-mode images.

Referring now to FIG. 7, the quality value 60 associated with each E-mode image 42 may further be used by a sequence combiner 85 (combining the quality values 60 of the E-mode images 42) to accumulate the overall quality 86 for a sequence of echo fields 28 acquired continuously. The overall quality 86 provides additional feedback to operators or can be used for training purposes.

These techniques are not limited to use with data acquired with ultrasound machines, but can be used with other image modalities as will be understood to those of ordinary skill in the art. It is specifically intended that the present invention not be limited to the embodiments and illustrations contained herein, but include modified forms of those embodiments including portions of the embodiments and combinations of elements of different embodiments as come within the scope of the following claims.

What we claim is:

1. An E-mode imaging apparatus comprising:
   (a) a probe containing an ultrasound transducer for (i) transmitting ultrasonic beams toward a material to be image and (ii) receiving ultrasound echo signals produced by the ultrasonic beams to provide electrical echo signals;
   (b) an interface circuitry programmed to receive and process the electrical echo signals to provide digital values;
   (c) a processor for receiving the digital values and producing a series of echo images imaged during different stages of deformation of the material to be imaged, each image comprised of multiple image values;
   (d) a memory for storing the image values of the series of echo images and a stored operating program; and
   (e) an operator interface communicating with the processor to communicate a quality value of the image values to an operator manipulating the probe;
   wherein the processor receives the image values of the series of echo images and executes the stored operating program held in a non-transient medium to calculate:
   (i) E-mode data indicating a stiffness of the material determined from displacement of corresponding elements of the material represented in image values between different images;
   (ii) a quality value indicating a quality of E-mode data wherein the quality value is a combination of two different evaluations of the image values of two images, a first evaluation indicating a similarity of corresponding image values in the two images providing a higher first evaluation value when the similarity increases and a second evaluation indicating a degree of variation in values of an E-mode image formed of the image values of the two images provides a higher second evaluation value when the degree of variation increases;
   wherein the quality value increases as the first evaluation value increases and as the second evaluation value increases.

2. The E-mode imaging apparatus of claim 1 further including an operator interface providing a representation of the quality value selected from the group consisting of: a displayed number, a displayed visual gauge, a displayed indicator light, an audio signal.

3. The E-mode imaging apparatus of claim 2 wherein the first evaluation is a correlation.

4. The E-mode imaging apparatus of claim 3 wherein the correlation is between a first image and a warping of a second image according to displacements used to determine the E-mode images from the image data.

5. The E-mode imaging apparatus of claim 4 wherein the second evaluation is an evaluation indicating an information content of an E-mode image formed of the two images.

6. The E-mode imaging apparatus of claim 5 wherein the information content is determined from an entropy of an E-mode image formed of the two images.

7. The E-mode imaging apparatus of claim 6 wherein the quality value is a combination of three different evaluations of the image values of three images, wherein the third evaluation indicates a similarity of corresponding image values in two &mode images formed from the three images.

8. The E-mode imaging apparatus of claim 7 wherein the third evaluation is selected from the group consisting of correlation and mutual information of the image values of the two E-mode images.

* * * * *